United States Patent [19]

Buchecker et al.

[11] Patent Number: 5,264,149

[45] Date of Patent: Nov. 23, 1993

[54] LIQUID CRYSTAL COMPOUNDS HAVING A TERMINAL 1-ALKYNYL RESIDUE

[75] Inventors: Richard Buchecker, Zurich; Martin Schadt, Seltisberg, both of Switzerland; Frank Seils, Wieslet, Fed. Rep. of Germany

[73] Assignee: Hoffmann-La Roche Inc., Nutley, N.J.

[21] Appl. No.: 879,629

[22] Filed: May 7, 1992

Related U.S. Application Data

[62] Division of Ser. No. 579,905, Sep. 10, 1990, Pat. No. 5,171,473.

[30] Foreign Application Priority Data

Oct. 18, 1989 [CH] Switzerland ............... 3781/89
Jun. 26, 1990 [CH] Switzerland ............... 2146/90

[51] Int. Cl.$^5$ ............... C09K 19/06; C09K 19/34; C09K 19/30; C07D 319/06
[52] U.S. Cl. ............... 252/299.6; 252/299.61; 252/299.63; 585/25; 549/369; 549/372
[58] Field of Search ........... 252/299.01, 299.6, 299.61, 252/299.63; 359/103, 104; 585/20, 25; 549/369, 372

[56] References Cited

U.S. PATENT DOCUMENTS

| | | | |
|---|---|---|---|
| 4,528,114 | 7/1985 | Petrzilka | 252/299.6 |
| 4,613,208 | 9/1986 | Boller et al. | 359/103 |
| 4,621,901 | 11/1986 | Petrzilka et al. | 359/103 |
| 4,830,470 | 5/1989 | Buchecker et al. | 359/104 |
| 5,171,473 | 12/1992 | Buchecker et al. | 252/299.61 |

FOREIGN PATENT DOCUMENTS

| | | |
|---|---|---|
| 122389 | 10/1985 | European Pat. Off. . |
| 167912 | 9/1987 | European Pat. Off. . |
| 268198 | 5/1988 | European Pat. Off. . |
| 315014 | 5/1989 | European Pat. Off. . |
| 3906019 | 9/1989 | Fed. Rep. of Germany . |
| 2216523 | 10/1989 | United Kingdom . |

*Primary Examiner*—Robert L. Stoll
*Assistant Examiner*—Shean C. Wu
*Attorney, Agent, or Firm*—George M. Gould; George W. Johnston

[57] ABSTRACT

Compounds of the formula

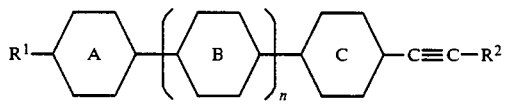

wherein n stands for the number 0 or 1; rings A, B and C each independently represent trans-1,4-cyclohexylene, trans-1,3-dioxane-2,5-diyl or unsubstituted or fluoro-substituted 1,4-phenylene; $R^1$ denotes 3E-alkenyl with 4 to 12 carbon atoms, 4-alkenyl with 5 to 12 carbon atoms or, when ring A represents trans-1,4-cyclohexylene or trans-1,3-dioxane-2,5-diyl, also 1E-alkenyl with 2 to 12 carbon atoms; and $R^2$ is hydrogen or $C_1$–$C_{10}$-alkyl, their manufacture as well as liquid crystalline mixtures which contain such compounds and their use for electro-optical purposes.

15 Claims, No Drawings

LIQUID CRYSTAL COMPOUNDS HAVING A TERMINAL 1-ALKYNYL RESIDUE

This is a division of application Ser. No. 07/579,905 filed Sep. 10, 1990, now U.S. Pat. No. 5,171,473.

FIELD OF THE INVENTION

The present invention is concerned with novel compounds having a terminal 1-alkynyl residue, their manufacture, liquid crystalline mixtures which contain such compounds and their use for electro-optical purposes.

BACKGROUND OF THE INVENTION

Liquid crystals are used primarily as dielectrics in indicating devices, since the optical properties of such substances can be influenced by an applied voltage. Electro-optical devices based on liquid crystals are well-known to the person skilled in the art and can be based on various effects. Such devices are, for example, cells having dynamic scattering, DAP cells (deformation of aligned phases), guest/host cells, TN Cells having a twisted nematic structure, STN cells ("super-twisted nematic"), SBE cells ("super-birefringence effect") and OMI cells ("optical mode interference"). The most common indicating devices are based on the Schadt-Helfrich effect and have a twisted nematic structure.

The liquid crystal materials must have a good chemical and thermal stability and a good stability towards electric fields and electromagnetic radiation. Further, at the usual operating temperatures they should have a suitable mesophase in as broad a range as possible (for example a nematic or a cholesteric phase for the cells referred to above), but nevertheless should have a sufficiently low viscosity and in the cells should give rise to short response times, low threshold potentials and a high contrast. Further properties such as the electrical conductivity, the dielectric anisotropy and the optical anisotropy must fulfil different requirements depending on the field of application and type of cell. For example, materials for cells having a twisted nematic structure should have a positive dielectric anisotropy and an electrical conductivity which is as low as possible.

In order to fulfil these to some extent contradictory requirements, it is generally necessary to produce mixtures having up to about 15 components. It is therefore important that the components have a good miscibility with one another and a sufficient solubility.

In order to achieve sufficiently broad mesophase ranges, it is usually necessary to add clearing point-increasing components to the mixtures, but in this case the viscosity and the electro-optical properties can be influenced disadvantageously. Further, materials having a low optical anisotropy, which are of interest e.g. for actively-addressed liquid crystal indicators, frequently produce smectic tendencies and usually also lead to an increase in the threshold potential, in the viscosity and/or in the response times. Furthermore, non-polar materials having a high optical anisotropy often have only smectic mesophases or even no liquid crystalline properties.

SUMMARY OF THE INVENTION

The invention is concerned with compounds of formula

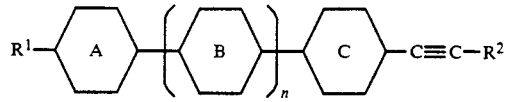

wherein n stands for the number 0 or 1; rings A, B and C each independently represent trans-1,4-cyclohexylene, trans-1,3-dioxane-2,5-diyl or unsubstituted or fluoro-substituted 1,4-phenylene; $R^1$ is a 3E-alkenyl with 4 to 12 carbon atoms, a 4-alkenyl with 5 to 12 carbon atoms or when ring A represents trans-1,4-cyclohexylene or trans-1,3-dioxane-2, 5-diyl, also a 1E-alkenyl with 2 to 12 carbon atoms; and $R^2$ is hydrogen or $C_1$-$C_{10}$-alkyl.

DETAILED DESCRIPTION OF THE INVENTION

The invention is concerned with compounds of formula

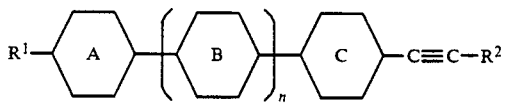

wherein n stands for the number 0 or 1; rings A, B and C each independently represent trans-1,4-cyclohexylene, trans-1,3-dioxane-2,5-diyl or unsubstituted or fluoro-substituted 1,4-phenylene; $R^1$ is a 3E-alkenyl with 4 to 12 carbon atoms, a 4-alkenyl with 5 to 12 carbon atoms or when ring A represents trans-1,4-cyclohexylene or trans-1,3-dioxane-2, 5-diyl, also a 1E-alkenyl with 2 to 12 carbon atoms; and $R^2$ is hydrogen or $C_1$-$C_{10}$-alkyl.

The compounds in accordance with the invention are non-polar compounds with comparatively very broad mesophase ranges, high clearing points and a pronounced nematic tendency. In spite of the high clearing points, they have a remarkably low viscosity and favorable electro-optical properties, in particular they permit short switching times, low threshold potentials and, depending on the choice of $R^1$, a modification of the elastic properties. Further, the optical anisotropy can be varied in a broad range; for example, the compounds of formula I in which rings A, B and C are trans-1,4-cyclohexylene and/or trans-1,3-dioxane-2,5-diyl have low optical anisotropies and the compounds of formula I in which rings A, B and C are unsubstituted or fluoro-substituted 1,4-phenylene have especially high optical anisotropies.

Having regard to the excellent properties, the compounds in accordance with the invention also offer the possibility of decreasing the number of components in a mixture and thus of simplifying the mixture substantially. In this case it is of advantage that the compounds in accordance with the invention have a good miscibility with known materials and, having regard to the low melting enthalpies, also have a good solubility in high concentrations.

The above term "fluoro-substituted 1,4-phenylene" embraces in the scope of the present invention especially 2-fluoro-1,4-phenylene and 2,3-difluoro-1,4-phenylene.

The term "1E-alkenyl with 2 to 12 carbon atoms" embraces straight-chain or branched residues, especially the straight-chain residues vinyl, 1E-propenyl, 1E-butenyl, 1E-pentenyl, 1E-hexenyl, 1E-heptenyl, 1E-octenyl, 1E-nonenyl, 1E-decenyl, 1E-undecenyl and 1E-dodecenyl.

The term "3E-alkenyl with 4 to 12 carbon atoms" embraces straight-chain or branched residues, especially the straight-chain residues 3-butenyl, 3E-pentenyl, 3E-hexenyl, 3E-heptenyl, 3E-octenyl, 3E-nonenyl, 3E-decenyl, 3E-undecenyl and 3E-dodecenyl.

The term "4-alkenyl with 5 to 12 carbon atoms" embraces straight-chain or branched residues, especially the straight-chain residues 4-pentenyl, 4-hexenyl, 4-heptenyl, 4-octenyl, 4-nonenyl, 4-decenyl, 4-undecenyl and 4-dodecenyl. 4-pentenyl and the Z-isomers of the other named residues are preferred.

The term "$C_1$–$C_{10}$-alkyl" embraces straight-chain and branched residues, especially the straight-chain residues methyl, ethyl, propyl, butyl, pentyl, hexyl, heptyl, octyl, nonyl and decyl.

The term "saturated ring" denotes in the scope of the present invention trans-1,4-cyclohexylene and trans-1,3-dioxane-2,5-diyl. The term "aromatic ring" denotes unsubstituted or fluoro-substituted 1,4-phenylene, especially 1,4-phenylene, 2-fluoro-1,4-phenylene and 2,3-difluoro-1,4-phenylene.

Compounds of formula I in which $R^1$ is a straight-chain residue and $R^2$ is hydrogen or a straight-chain residue are preferred However, if desired, $R^1$ and/or $R^2$ can have a chain branching. For example, compounds of formula I having a chiral residue $R^1$ and/or $R^2$ are suitable as optically active dopants for the production of cholesteric phases.

In formula I preferably a maximum of one of rings A, B and C (preferably ring A or B) stands for trans-1,3-dioxane-2,5-diyl.

Preferably, the compounds of formula I have a maximum of 1 or 2 lateral fluorine substituents. Any fluorine substituents which may be present are preferably on ring B or especially on ring C.

A preferred aspect is concerned with those compounds of formula I in which ring A is a saturated ring and ring C is an aromatic ring. Where n=1, ring B can be saturated or aromatic.

A further preferred aspect is concerned with those compounds of formula I in which rings A and C represent saturated rings. Where n=1, ring B is preferably also a saturated ring. Especially preferred are those compounds in which one of the rings (especially ring A or B) stands for trans-1,4-cyclohexylene or trans-1,3-dioxane-2,5-diyl and the other rings stand for trans-1,4-cyclohexylene. These compounds have very low optical anisotropies.

Furthermore, those compounds of formula I in which rings A and C represent aromatic rings are preferred. Where n=1, ring B is preferably also an aromatic ring. These compounds have especially high optical anisotropies.

Examples of especially preferred sub-groups of compounds of formula I are the compounds of formulas

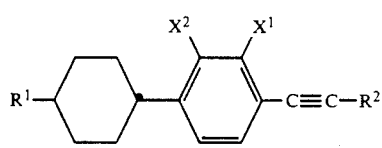

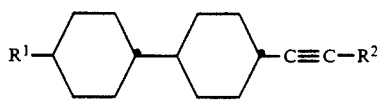

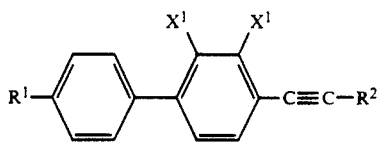

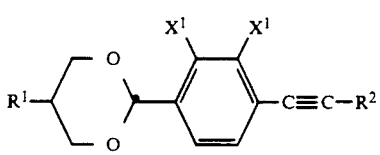

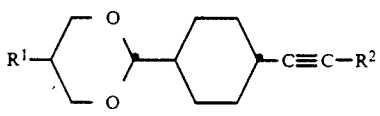

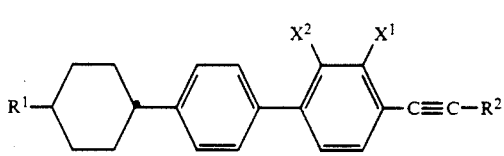

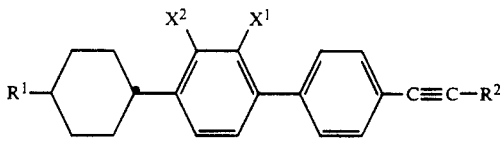

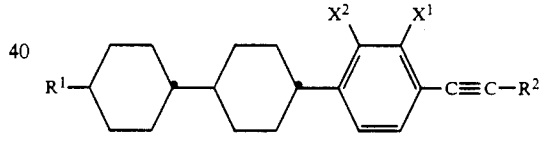

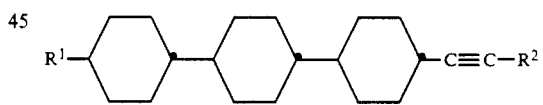

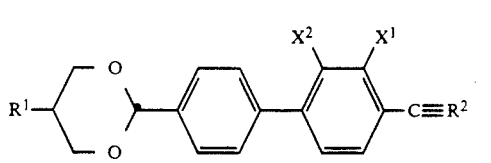

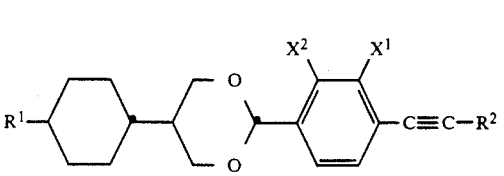

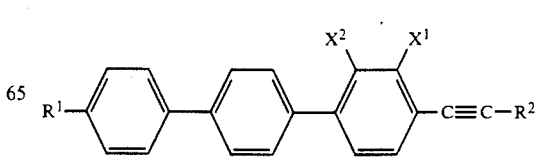

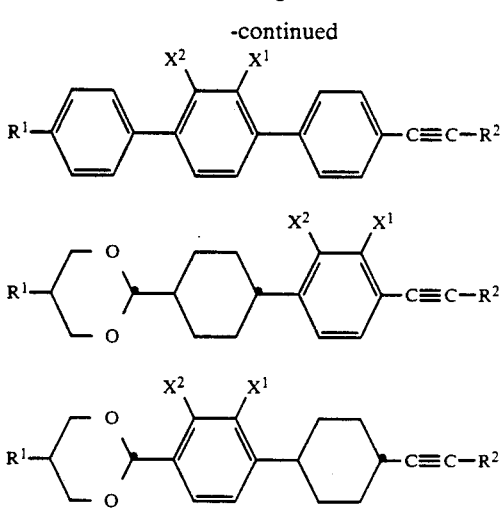

wherein $X^1$ and $X^2$ each independently represent hydrogen or fluorine; $R^2$ is hydrogen or $C_1$-$C_{10}$-alkyl; and $R^1$ denotes 3E-alkenyl with 4 to 12 carbon atoms, 4-alkenyl with 5 to 12 carbon atoms and in formulas I-1, I-2, I-4, I-5, I-6, I-7, I-8, I-9, I-10, I-11, I-14 and I-15 $R^1$ also is 1E-alkenyl with 2 to 12 carbon atoms.

Preferably, $R^1$ in the above formulas has a maximum of 7 carbon atoms. Residues $R^1$ with up to 5 carbon atoms are especially preferred.

$R^2$ in the above formulas preferably is hydrogen or $C_1$-$C_5$-alkyl, especially hydrogen or $C_1$-$C_3$-alkyl.

The compounds of formula I can be manufactured in accordance with the invention by a) for the manufacture of the compounds of formula I in which $R^2$ is hydrogen, reacting a compound of formula

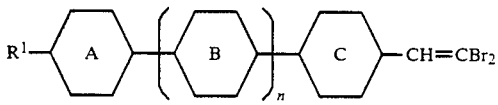

wherein n, $R^1$ and rings A, B and C have the significances given in formula I, with an alkyllithium, or b) for the manufacture of the compounds of formula I in which $R^2$ is $C_1$-$C_{12}$-alkyl, alkylating a compound of formula I in which $R^2$ is hydrogen.

The reaction of a compound of formula II with an alkyllithium can be effected in a manner known per se. Preferred lithium compounds are $C_1$-$C_4$-alkyllithiums such as methyllithium, butyllithium and the like. The reaction is preferably effected in an inert organic solvent such as hexane, tetrahydrofuran and the like at maximum temperatures of about $-70°$ C.

The alkylation of the compounds of formula I in which $R^2$ is hydrogen can be effected according to usual alkylation methods. According to a preferred method the acetylene compound is deprotonized with a base and then alkylated with a $C_1$-$C_{10}$-alkyl halide. The deprotonization can be effected, for example, with butyllithium, methyllithium, sodium hydride and the like in an inert organic solvent (e.g. hexane, tetrahydrofuran and the like) at temperatures below about $-30°$ C. The subsequent alkylation step can be carried out, for example, with an alkyl chloride, bromide or iodide in the presence of hexamethylphosphoric acid triamide.

The compounds of formula II are novel. They can be prepared in a manner known per se from the cyano compounds of formula

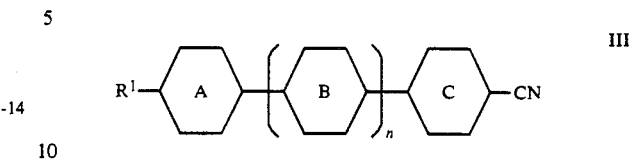

wherein n, $R^1$ and rings A, B and C have the significances given in formula I.

For example, a compound of formula III can be reduced with diisobutylaluminium hydride and the aldehyde obtained can be reacted with tetrabromomethane and triphenylposphine to give a compound of formula II.

The compounds of formula III are known or are analogues of known compounds and can be prepared according to the methods described in EP-A-0122389, EP-A-0167912 and EP-A-0315050.

The compounds of formula I can be used in the form of mixtures with one another and/or with other liquid crystal components such as e.g. with substances from the classes of Schiff's bases, azobenzenes, azoxybenzenes, phenylbenzoates, cyclohexanecarboxylic acid phenyl esters, cyclohexanecarboxylic acid cyclohexyl esters, biphenyls, henylcyclohexanes, cyclohexylcyclohexanes, phenylpyrimidines, cyclohexylpyrimidines, phenyldioxanes, 2-cyclohexyl-1-phenylethanes, terphenyls, cyclohexylbiphenyls, cyclohexylphenylpyrimidines and the like. Such substances are known to the person skilled in the art and many of them are, moreover, commercially available.

The liquid crystalline mixtures in accordance with the invention contain at least two components, of which at least one component is a compound of formula I. A second component and optionally further components can be further compounds of formula I and/or other liquid crystal components.

The compounds of formula I are especially suitable for nematic mixtures or, insofar as at least one component of the mixture is optically active, also for cholesteric mixtures. A preferred field of application is their use as dielectrics in liquid crystal indicating devices having a twisted nematic liquid crystal structure such as TN cells, STN cells, SBE cells and OMI cells. Preferred mixtures are therefore those which contain one or more compounds of formula I and one or more compounds having positive dielectric anisotropy.

Having regard to the good solubility of the compounds of formula I in other liquid crystal materials and having regard to their good miscibility with one another, the amount of the compounds of formula I in the mixtures in accordance with the invention can be relatively high and can amount to, for example, about 1-70 wt. % or above. In general, an amount of about 3-50 wt. %, especially about 5-30 wt. %, of compounds of formula I is preferred.

Preferably, the mixtures in accordance with the invention contain, in addition to one or more compounds of formula I, one or more compounds from the group of compounds of formulas

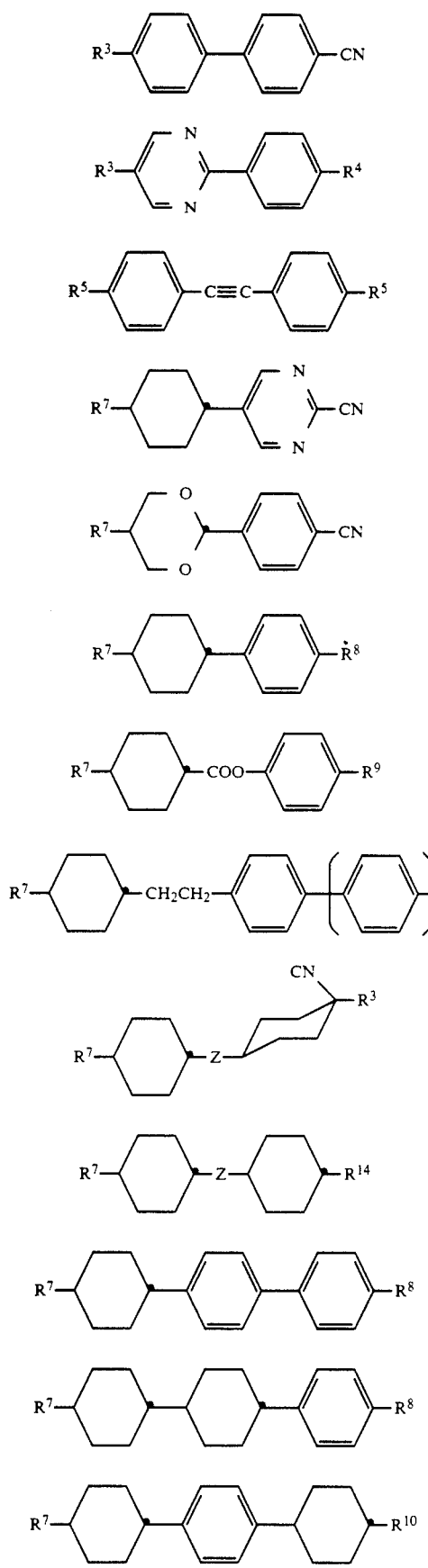
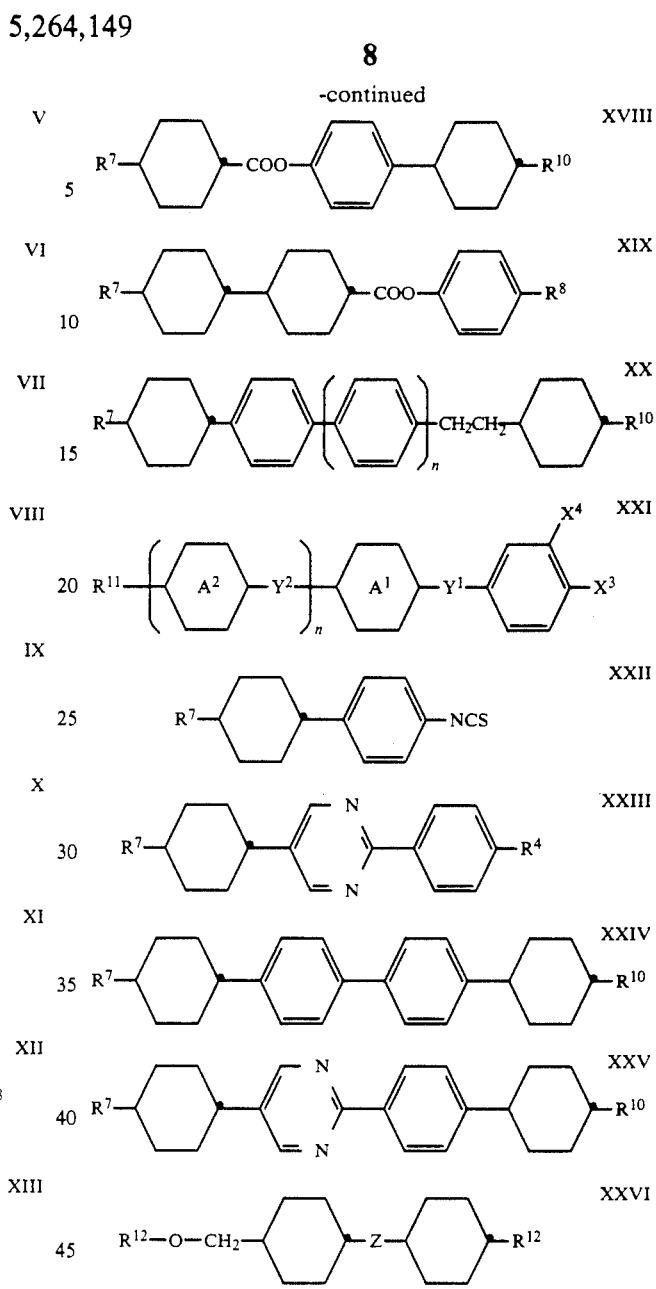

wherein $R^3$ is alkyl, 3E-alkenyl or 4-alkenyl; $R^4$ represents alkyl, cyano or fluorine; $R^5$ and $R^6$ denote alkyl or alkoxy; $R^7$ and $R^{10}$ each independently are alkyl, 1E-alkenyl, 3E-alkenyl or 4-alkenyl; $R^8$ denotes cyano, alkyl, 3E-alkenyl, 4-alkenyl, alkoxy, 2E-alkenyloxy or 3-alkenyloxy; $R^9$ is alkoxy, 2E-alkenyloxy or 3-alkenyloxy; n stands for the number 0 or 1; Z represents a single covalent bond or —CH$_2$CH$_2$—; $X^3$ denotes fluorine or chlorine and $X^4$ denotes hydrogen, fluorine or chlorine; $R^{11}$ is alkyl, 3E-alkenyl, 4-alkenyl, alkoxy, 2E-alkenyloxy or 3-alkenyloxy; one of the groups $Y^1$ and $Y^2$ is a single covalent bond, —COO—, —OOC—, —CH$_2$CH$_2$—, —CH$_2$O— or —OCH$_2$— and the other of the groups $Y^1$ and $Y^2$ is a single covalent bond; rings $A^1$ and $A^2$ each independently represent substituted or unsubstituted trans-1,4-cyclohexylene in which optionally 2 non-adjacent CH$_2$ groups are replaced by oxygen or substituted or unsubstituted 1,4-phenylene in which optionally 1 CH group or 2 CH groups is/are replaced by nitrogen; $R^{12}$ denotes alkyl or 2-alkenyl; $R^{13}$ is 1E-alkenyl, 3E-alkenyl, 4-alkenyl, (2-alkenyl)oxymethyl, alkyl or cyano; and $R^{14}$ denotes cyano, alkyl, 1E-alkenyl, 3E-alkenyl, 4-alkenyl, alkoxy, 2E-alkenyloxy or 3-alkenyloxy.

The term "substituted or unsubstituted trans-1,4-cyclohexylene in which optionally 2 non-adjacent $CH_2$ groups are replaced by oxygen" embraces especially trans-1,4-cyclohexylene and trans-1,3-dioxane-2,5-diyl as well as rings which are substituted with substituents which are usual in liquid crystals such as cyano, methyl, fluorine or chlorine, for example 1-cyano-trans-1,4-cyclohexylene or 2-methyl-trans-1,4-cyclohexylene.

The term "substituted or unsubstituted 1,4-phenylene in which optionally 1 CH group or 2 CH groups is/are replaced by nitrogen" embraces especially 1,4-phenylene, pyridine-2,5-diyl, pyrazine-2,5-diyl and pyrimidine-2,5-diyl as well as rings which are substituted with substituents which are usual in liquid crystals such as cyano, methyl, fluorine or chlorine, for example 2-cyano-1,4-phenylene, 2-fluoro-1,4-phenylene, 2-chloro-1,4-phenylene or 2-methyl-1,4-phenylene.

Preferred mixture components having positive dielectric anisotropy are the cyano- and halo-compounds of formulas V, VI, VIII, IX, X, XII, XIV, XV, XVI, XIX, XXI and XXIII as well as the isothiocyanates of formula XXII. Preferably, the final mixture contains about 20-70 wt. %, especially about 25-50 wt. %, of one or more of these compounds.

The mixtures in accordance with the invention can also contain optically active compounds (e.g. optically active 4'-alkyl- or 4'-alkoxy-4-biphenylcarbonitriles) and/or dichroic coloring substances (e.g. azo, azoxy or anthraquinone coloring substances). The amount of such compounds is determined by the solubility, the desired pitch, colour, extinction and the like. In general, the amount of optically active compounds and dichroic coloring substances amounts to a maximum of in each case about 10 wt. % in the final mixture.

The manufacture of the mixtures in accordance with the invention and the manufacture of the electro-optical devices can be effected in a manner known per se.

The manufacture of the compounds of formula I and of liquid crystalline mixtures containing these compounds are illustrated in more detail by the following Examples. C is a crystalline phase, S is a smectic phase, $S_A$ is a smectic A phase, N is a nematic phase and I is the isotropic phase. $V_{10}$ denotes the voltage for 10% transmission (viewing direction perpendicular to the surface of the plates). $t_{on}$ and $t_{off}$ denote respectively the switching-on time and the switching-off time, $\Delta n$ denotes the optical anisotropy and $\Delta H$ denotes the melting enthalpy.

EXAMPLE 1 a) A solution of 9.036 g of trans-4-[trans-4-(1E-propenyl)cyclohexyl]cyclohexanecarbonitrile in 45 ml of toluene was treated dropwise while gassing with nitrogen at 0°-4° C. within 55 minutes with 39 ml of a 20 percent (v/v) solution of diisobutylaluminium hydride in toluene. After completion of the addition the reaction mixture was stirred at 0° C. for a further 15 minutes and then at room temperature for a further 3.5 hours. Subsequently, the colourless reaction solution was pipetted into 200 ml of 1N sulphuric acid while cooling with an ice bath and the mixture obtained was extracted once with 400 ml of methylene chloride and twice with 150 ml of methylene chloride each time. The combined methylene chloride phases were washed twice with 150 ml of water each time, dried over sodium sulphate, filtered and evaporated. There were thus obtained 10.2 g of crude trans-4-[trans-4-(1E-propenyl)cyclohexyl]cyclohexanecarboxaldehyde as a colourless oil.

b) A solution of 28.5 g of tetrabromomethane in 519 ml of methylene chloride was treated dropwise while gassing with nitrogen at −15° C. within 13 minutes with a solution of 45.7 g of triphenylphosphine in 97 ml of methylene chloride. The orange solution was stirred at about −10° C. for a further 10 minutes and then treated dropwise within 25 minutes with a solution of 10.2 g of trans-4-[trans-4-(1E-propenyl)cyclohexyl]cyclohexanecarboxaldehyde in 112 ml of methylene chloride and rinsed with 25 ml of methylene chloride. The reaction mixture was stirred at about 0° C. for a further 50 minutes and then poured into 3.9 l of hexane. The mixture was stirred at room temperature for 2.5 hours. Thereafter, the precipitate was filtered off under suction and washed with hexane. The filtrate was concentrated in a vacuum and the yellowish solid residue obtained (33.4 g) was suspended in 2 l of hexane. The suspension was stirred at room temperature for 15 minutes and then cooled in an ice bath for 1 hour. Subsequently, the precipitate was filtered off under suction and washed with about 0.5 l of cold hexane. The filtrate was concentrated in a vacuum. The colourless solid residue (19.2 g, was purified by chromatography on silica gel with hexane at 0.4 bar. There were thus obtained 12.7 g of trans-4-(2,2-dibromovinyl)-1-[trans-4-(1E-propenyl)cyclohexyl]cyclohexane as a colourless solid substance.

c) A solution of 12.7 g of trans-4-(2,2-dibromovinyl)-1-[trans-4-(1E-propenyl)cyclohexyl]cyclohexane in 500 ml of tetrahydrofuran was treated dropwise while gassing with nitrogen at −74° C. within 30 minutes with 49 ml of a 1.6M solution of butyllithium in hexane. The yellowish solution was stirred at −74° C. for a further 1 hour, then poured into 500 ml of water and extracted once with 400 ml of hexane and twice with 200 ml of hexane each time. The combined hexane phases were washed twice with 200 ml of water each time, dried over sodium sulphate, filtered and evaporated. There were thus obtained 7.9 g of trans-4-ethynyl-1-[trans-4-(1E-propenyl)cyclohexyl]cyclohexane as colourless crystals. Recrystallization from methylene chloride/methanol gave pure product with m.p. (C-N) 45.1° C., cl.p. (N-I) 88.9° C. and $\Delta H = 2.323$ kcal/mol.

The following compounds can be manufactured in an analogous manner:

trans-4-Ethynyl-1-[trans-4-(3-butenyl)cyclohexyl]cyclohexane, m.p. (C-N) 9.0° C. (supercoolable to about −40° C.), cl.p. (N-I) 64.8° C., $\Delta H = 2.280$ kcal/mol;

trans-4-ethynyl-1-[trans-4-(3E-pentenyl)cyclohexyl]cyclohexane, m.p (C-N) 27.6° C., cl.p. (N-I) 87.7° C., $\Delta H = 3.207$ kcal/mol;

trans-4-ethynyl-1-[trans-4-(4-pentenyl)cyclohexyl]cyclohexane, m.p (C-N) 12.7° C., cl.p. (N-I) 41.5° C., $\Delta H = 4.526$ kcal/mol;

4-ethynyl-1-[trans-4-(1E-propenyl)cyclohexyl]benzene;
4-ethynyl-1-[trans-4-(3E-pentenyl)cyclohexyl]benzene;
4-ethynyl-1-[trans-4-(4-pentenyl)cyclohexyl]benzene;
4'-ethynyl-4-[trans-4-(1E-propenyl)cyclohexyl]biphenyl;
4'-ethynyl-4-[trans-4-(3E-pentenyl)cyclohexyl]biphenyl;
4'-ethynyl-4-[trans-4-(4-pentenyl)cyclohexyl]biphenyl;
4-ethynyl-1-[trans-4-[trans-4-(1E-propenyl)cyclohexyl]cyclohexyl]benzene;
4-ethynyl-4'-(3-butenyl)biphenyl;

4-ethynyl-4'-(4-pentenyl)biphenyl;
4-ethynyl-2,3-difluoro-4'-(3-butenyl)biphenyl;
4-ethynyl-2,3-difluoro-4'-(4-pentenyl)biphenyl;
4-ethynyl-1-[trans-5-(3-butenyl)-1,3-dioxan-2-yl]benzene;
4-ethynyl-1-[trans-5-(4-pentenyl)-1,3-dioxan-2-yl]benzene;
4-ethynyl-4'-[trans-5-(3-butenyl)-1,3-dioxan-2-yl]biphenyl;
4-ethynyl-1-[trans-4-[trans-5-(3-butenyl)-1,3-dioxan-2-yl]cyclohexyl]benzene;
4-ethynyl-1-[trans-5-[trans-4-(1E-propenyl)cyclohexyl]-1,3-dioxan-2-yl]benzene;
4-(trans-4-ethynylcyclohexyl)-1-[trans-5-(1E-propenyl)-1,3-dioxan-2-yl]benzene.

EXAMPLE 2

A solution of 1.0 g of trans-4-ethynyl-1-[trans-4-(1E-propenyl)cyclohexyl]cyclohexane in 39 ml of tetrahydrofuran was treated dropwise while gassing with nitrogen at −26° C. within 3 minutes with 3.1 ml of a 1.6M solution of butyllithium in hexane. The yellowish solution was stirred at −20° C. for a further 30 minutes, then treated with 4.3 ml of hexamethylphosphoric acid triamide and subsequently with 0.696 g of propyl bromide. The reaction mixture was stirred at room temperature for a further 3.5 hours, then poured into 65 ml of water and subsequently extracted once with 50 ml of hexane and twice with 40 ml of hexance each time. The combined hexane phases were washed twice with 30 ml of water each time, dried over sodium sulphate, filtered and evaporated. The yellowish nematic crude product (1.186 g) was purified by chromatography on silica gel with hexane at 0.4 bar. There were thus obtained 1.088 g of trans-4-(1-pentynyl)-1-[trans-4-(1E-propenyl)cyclohexyl]cyclohexane as a colourless nematic substance. Recrystallization from diethyl ether/methanol gave 0.805 g of pure product with m.p. (C-N) 28.1° C., cl.p. (N-I) 68.6° C. and $\Delta H = 5.602$ kcal/mol.

The following compounds can be manufactured in an analogous manner:

trans-4-(1-Propynyl)-1-[trans-4-(1E-propenyl cyclohexyl]cyclohexane, m.p. (C-N) 69.2° C., cl.p. (N-I) 117.7° C., $\Delta H = 2.310$ kcal/mol;

trans-4-(1-butynyl)-1-[trans-4-(1E-propenyl)cyclohexyl]cyclohexane, m.p. (C-N) 26.8° C., cl.p. (N-I) 82.1° C., $\Delta H = 4.430$ kcal/mol;

trans-4-(1-propynyl)-1-[trans-4-(3-butenyl)cyclohexyl]cyclohexane, m.p. (C-N) 9.2° C., cl.p. (N-I) 71.5° C.; $\Delta H = 3.714$ kcal/mol;

trans-4-(1-butynyl)-1-[trans-4-(3-butenyl)cyclohexyl]cyclohexane, m.p. (C-N) 6.8° C., cl.p. (N-I) 52.5° C., $\Delta H = 4.522$ kcal/mol;

trans-4-(1-propynyl)-1-[trans-4-(3E-pentenyl)cyclohexyl]cyclohexane, m.p. (C-N) 47.5° C., cl.p. (N-I) 105.5° C., $\Delta H = 4.594$ kcal/mol;

trans-4-(1-butynyl)-1-[trans-4-(3E-pentenyl)cyclchexyl]cyclohexane, m.p. (C-N) 22.8° C., cl.p. (N-I) 86.5° C., $\Delta H = 4.406$ kcal/mol;

trans-4-(1-pentynyl)-1-[trans-4-(3E-pentenyl)cyclohexyl]cyclohexane, m.p. (C-N) 35.8° C., cl.p. (N-I) 77.9° C., $\Delta H = 4.160$ kcal/mol;

trans-4-(1-hexynyl)-1-[trans-4-(3E-pentenyl)cyclohexyl]cyclohexane, m.p. (C-N) 34.5° C., cl.p. (N-I) 55.5° C., $\Delta H = 5.058$ kcal/mol;

trans-4-(1-propynyl)-1-[trans-4-(4-pentenyl)cyclohexyl]cyclohexane, m.p. (C-N) 28.8° C., cl.p. (N-I) 61.3° C., $\Delta H = 5.418$ kcal/mol;

trans-4-(1-butynyl)-1-[trans-4-(4-pentenyl)cyclohexyl]cyclohexane, m p. (C-N) 6.6° C., cl.p. (N-I) 44.5° C., $\Delta H = 4.168$ kcal/mol;

trans-4-(1-pentynyl)-1-[trans-4-(4-pentenyl)cyclohexyl]cyclohexane, m.p. (C-N) −11.0° C., cl.p. (N-I) 58.9° , $\Delta H = 3.366$ kcal/mol;

4-(1-propynyl)-1-[trans-4-(1E-propenyl)cyclohexyl]benzene, m.p. (C-N) 69.4° C., cl.p (N-I) 90.7° C., $\Delta H = 4.509$ kcal/mol;

4-(1-propynyl)-1-[trans-4-(3E-pentenyl)cyclohexyl]benzene, m.p. (C-N) 48.6° C., cl.p. (N-I) 82.5° C., $\Delta H = 3.127$ kcal/mol;

4-(1-propynyl)-1-[trans-4-(4-pentenyl)cyclohexyl]benzene, m.p. (C-N) 13.9° C., cl.p. (N-I) 31.2° C., $\Delta H = 4.127$ kcal/mol;

4'-(1-propynyl)-4-[trans-4-(1E-propenyl)cyclohexyl]biphenyl, m.p. (C-N) 189° C., cl.p. (N-I) >300° C. (decomposition), $\Delta H = 5.443$ kcal/mol;

4'-(1-propynyl)-4-[trans-4-(3E-pentenyl)cyclohexyl]biphenyl, m.p. (C-$S_A$) 144.8° C., transition $S_A$-N 181.5° C., cl.p. (N-I) >266° C. (decomposition), $\Delta H = 4.490$ kcal/mol;

4-(1 propynyl)-1-[trans-4-[trans-4-(1E-propenyl)cyclohexyl]cyclohexyl]benzene;

4-(1-propynyl)-4'-(3-butenyl)biphenyl;
4-(1-propynyl)-4'-(4-pentenyl)biphenyl;
4-(1 propynyl)-2,3-difluoro-4'-(3-butenyl)biphenyl;
4-(1-propynyl)-2,3-difluoro-4'-(4-pentenyl)biphenyl;
4-(1-propynyl)-1-[trans-5-(3-butenyl)-1,3-dioxan-2-yl]benzene;
4-(1-propynyl)-1-[trans-5-(4-pentenyl)-1,3-dioxan-2-yl]benzene, m.p. (C-I) 68° C.;
4-(1-propynyl)-4'-[trans-5-(3-butenyl)-1,3-dioxan-2-yl]biphenyl, m.p. (C-N) 116.1° C., S-N 91° C., cl.p. (N-I) 235.7° C., $\Delta H = 4.971$ kcal/mol;
4-(1-propynyl)-1-[trans-4-[trans-5-(3-butenyl)-1,3-dioxan-2-yl]-cyclohexyl]benzene, m.p. (C-N) 131.5° C., cl.p. (N-I) 212.3° C., $\Delta H = 7.235$ kcal/mol;
4-(1-propynyl)-1-[trans-5-[trans-4-(1E-propenyl)cyclohexyl]-1,3-dioxan-2-yl]benzene;
4-[trans-4-(1-propynyl)cyclohexyl]-1-[trans-5-(1E-propenyl)-1,3-dioxan-2-yl]benzene.

EXAMPLE 3

Several binary mixtures were manufactured from 4-(trans-4-pentylcyclohexyl)benzonitrile and in each case one compound of formula I and the influence on clearing point, $V_{10}$, $t_{on}$, $t_{off}$ and $\Delta n$ is investigated. $V_{10}$, $t_{on}$ and $t_{off}$ were measured at 22° C. in a TN cell having a plate separation of 8 μm, with the 2.5-fold value of $V_{10}$ being chosen as the operating potential. $\Delta n$ was measured at 22° C. The components of formula I used, their concentration in the binary mixture and the measured data are set forth in Table 1. The corresponding values for pure 4-(trans-4-pentylcyclohexyl)benzonitrile are given for comparison.

TABLE 1

| Binary mixture with 4-(trans-4-pentylcyclohexyl)benzonitrile | | | | | |
| --- | --- | --- | --- | --- | --- |
| Component of formula I, concentration in wt. % | cl.p. (N-I) [°C.] | $v_{10}$ [volt] | $t_{on}$ [ms] | $t_{off}$ [ms] | $\Delta n$ |
| [100% 4-(trans-4-Pentylcyclohexyl)benzonitrile] | 54.6 | 1.62 | 30 | 42 | 0.120 |

TABLE 1-continued

| Binary mixture with 4-(trans-4-pentylcyclohexyl)benzonitrile | | | | | |
|---|---|---|---|---|---|
| Component of formula I, concentration in wt. % | cl.p. (N-I) [°C.] | $v_{10}$ [volt] | $t_{on}$ [ms] | $t_{off}$ [ms] | $\Delta n$ |
| 10% trans-4-Ethynyl-1-[trans-4-(1E-propenyl)-cyclohexyl]cyclohexane | 60.3 | 1.69 | 22 | 37 | 0.121 |
| 20% trans-4-Ethynyl-1-[trans-4-(1E-propenyl)-cyclohexyl]cyclohexane | 66.0 | 1.89 | 20 | 35 | 0.122 |
| 10% trans-4-(1-Propynyl)-1-[trans-4-(1E-propenyl)-cyclohexyl]cyclohexane | 56.2 | 1.70 | 20 | 36 | 0.122 |
| 20% trans-4-(1-Propynyl)-1-[trans-4-(1E-propenyl)-cyclohexyl]cyclohexane | 58.9 | 1.79 | 21 | 35 | 0.119 |
| 10% trans-4-(1-Propynyl)-1-[trans-4-(3E-pentenyl)-cyclohexyl]cyclohexane | 57.9 | 1.62 | 22 | 37 | 0.122 |
| 50% trans-4-(1-Propynyl)-1-[trans-4-(3E-pentenyl)-cyclohexyl]cyclohexane | 73.1 | 2.53 | 20 | 34 | 0.114 |
| 10% trans-4-(1-Butynyl)-1-[trans-4-(1E-propenyl)-cyclohexyl]cyclohexane | 53.9 | 1.62 | 20 | 36 | 0.118 |
| 20% trans-4-(1-Butynyl)-1-[trans-4-(1E-propenyl)-cyclohexyl]cyclohexane | 54.2 | 1.69 | 20 | 36 | 0.115 |
| 10% 4-(1-Propynyl)-1-[trans-4-(1E-propenyl)cyclo-hexyl]benzene | 57.0 | 1.60 | 21 | 36 | 0.128 |
| 50% 4-(1-Propynyl)-1-[trans-4-(1E-propenyl)cyclo-hexyl]benzene | 69.1 | 2.29 | 16 | 27 | >0.140 |
| 10% 4-(1-Propynyl)-1-[trans-4-(3E-pentenyl)cyclo-hexyl]benzene | 61.7 | 1.73 | 21 | 36 | 0.336 |
| 10% 4-(1-Propynyl)-1-[trans-4-(4-pentenyl)cyclo-hexyl]benzene | 52.7 | 1.47 | 22 | 39 | 0.122 |
| 10% 4'-(1-Propynyl)-4-[trans-4-(3E-pentenyl)cyclo-hexyl]benzene | 71.3 | 1.73 | 25 | 40 | 0.141 |

We claim:

1. A compound of formula

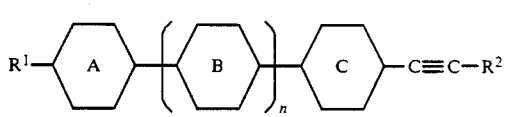

wherein n is the number 0 or 1; ring A is trans-1,4-cyclohexylene or trans-1,3-dioxane-2,5-diyl; rings B and C each independently are trans-1,4-cyclohexylene, trans-1,3-dioxane-2,5-diyl or unsubstituted or fluoro-substituted 1,4-phenylene; $R^1$ is 1E-alkenyl with 2 to 12 carbon atoms; and $R^2$ is hydrogen or $C_1$-$C_{10}$-alkyl, with the proviso that no more than one trans-1,3-dioxane-2,5-diyl ring is present.

2. The compound of claim 1, having the formula

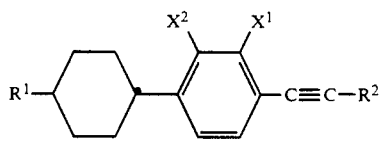

wherein $X^1$ and $X^2$ each independently are hydrogen or fluorine; $R^2$ is hydrogen or $C_1$-$C_{10}$-alkyl; and $R^1$ is 1E-alkenyl with 2 to 12 carbon atoms.

3. The compound of claim 1, having the formula

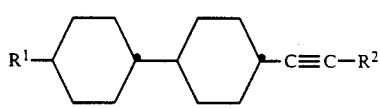

wherein $X^1$ and $X^2$ each independently are hydrogen or fluorine; $R^2$ is hydrogen or $C_1$-$C_{10}$-alkyl; and $R^1$ is 1E-alkenyl with 2 to 12 carbon atoms.

4. The compound of claim 1, having the formula

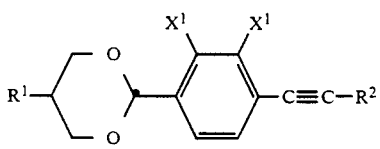

wherein $X^1$ and $X^2$ each independently are hydrogen or fluorine; $R^2$ is hydrogen or $C_1$-$C_{10}$-alkyl; and $R^1$ is 1E-alkenyl with 2 to 12 carbon atoms.

5. The compound of claim 1, having the formula

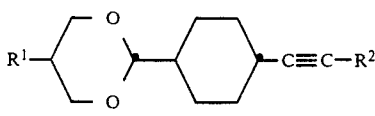

wherein $X^1$ and $X^2$ each independently are hydrogen or fluorine; $R^2$ is hydrogen or $C_1$-$C_{10}$-alkyl; and $R^1$ is 1E-alkenyl with 2 to 12 carbon atoms.

6. The compound of claim 1, having the formula

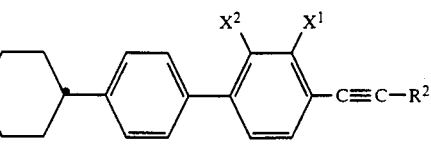

wherein $X^1$ and $X^2$ each independently are hydrogen or fluorine; $R^2$ is hydrogen or $C_1$-$C_{10}$-alkyl; and $R^1$ is 1E-alkenyl with 2 to 12 carbon atoms.

7. The compound of claim 1, having the formula

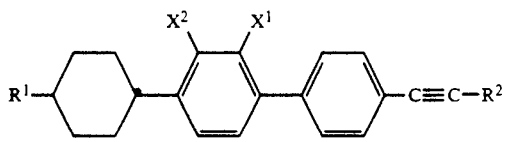

wherein $X^1$ and $X^2$ each independently are hydrogen or fluorine; $R^2$ is hydrogen or $C_1-C_{10}$-alkyl; and $R^1$ is 1E-alkenyl with 2 to 12 carbon atoms.

8. The compound of claim 1, having the formula

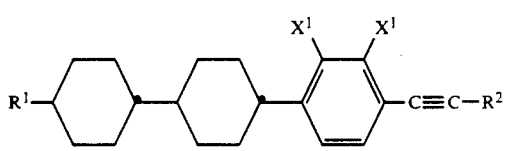

wherein $X^1$ and $X^2$ each independently are hydrogen or fluorine; $R^2$ is hydrogen or $C_1-C_{10}$-alkyl; and $R^1$ is 1E-alkenyl with 2 to 12 carbon atoms.

9. The compound of claim 1, having the formula

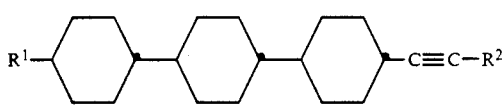

wherein $X^1$ and $X^2$ each independently are hydrogen or fluorine; $R^2$ is hydrogen of $C_1-C_{10}$-alkyl; and $R^1$ is 1E-alkenyl with 2 to 12 carbon atoms.

10. The compound of claim 1, having the formula

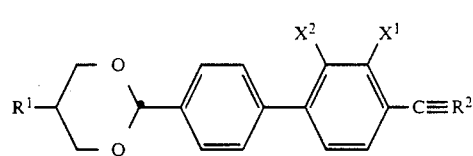

wherein $X^1$ and $X^2$ each independently are hydrogen or fluorine; $R^2$ is hydrogen or $C_1-C_{10}$-alkyl; and $R^1$ is 1E-alkenyl with 2 to 12 carbon atoms.

11. The compound of claim 1, having the formula

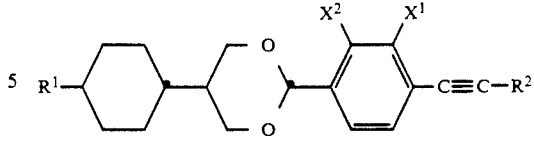

wherein $X^1$ and $X^2$ each independently are hydrogen or fluorine; $R^2$ is hydrogen or $C_1-C_{10}$-alkyl; and $R^1$ is 1E-alkenyl with 2 to 12 carbon atoms.

12. The compound of claim 1, having the formula

I-14 wherein $X^1$ and $X^2$ each independently are hydrogen or fluorine; $R^2$ is hydrogen or $C_1-C_{10}$-alkyl; and $R^1$ is 1E-alkenyl with 2 to 12 carbon atoms.

13. The compound of claim 1, having the formula

I-15 wherein $X^1$ and $X^2$ each independently are hydrogen or fluorine; $R^2$ is hydrogen or $C_1-C_{10}$-alkyl; and $R^1$ is 1E-alkenyl with 2 to 12 carbon atoms.

14. The compound of claim 1, wherein $R^1$ is 1E-propenyl.

15. A liquid crystalline mixture having at least two components, wherein at least one of such components is a compound of the formula

I wherein n is the number 0 or 1; ring A is trans-1,4-cyclohexylene or trans-1,3-dioxane-2,5-diyl; rings B and C each independently are trans-1,4-cyclohexylene, trans-1,3-dioxane-2,5-diyl or unsubstituted or fluoro-substituted 1,4-phenylene; $R^1$ is 1E-alkenyl with 2 to 12 carbon atoms; and $R^2$ is hydrogen or $C_1-C_{10}$-alkyl, with the proviso that no more than one trans-1,3-dioxane-2,5-diyl ring is present.

* * * * *